(12) United States Patent
Zhang et al.

(10) Patent No.: US 9,637,793 B2
(45) Date of Patent: May 2, 2017

(54) PANCREATIC CANCER MARKERS, AND DETECTING METHODS, KITS, BIOCHIPS THEREOF

(75) Inventors: Chenyu Zhang, Beijing (CN); Rui Liu, Beijing (CN); Cheng Wang, Beijing (CN); Yi Bai, Beijing (CN); Chunni Zhang, Beijing (CN); Ke Zeng, Beijing (CN)

(73) Assignee: Micromedmark Biotech Co., Ltd., Beijing (CN)

( * ) Notice: Subject to any disclaimer, the term of this patent is extended or adjusted under 35 U.S.C. 154(b) by 200 days.

(21) Appl. No.: 13/518,801

(22) PCT Filed: Dec. 24, 2009

(86) PCT No.: PCT/CN2009/001547
§ 371 (c)(1),
(2), (4) Date: Aug. 6, 2012

(87) PCT Pub. No.: WO2011/075873
PCT Pub. Date: Jun. 30, 2011

(65) Prior Publication Data
US 2013/0072393 A1    Mar. 21, 2013

(51) Int. Cl.
*C12Q 1/68*        (2006.01)
*C40B 40/06*       (2006.01)

(52) U.S. Cl.
CPC ............ *C12Q 1/6886* (2013.01); *C12Q 1/686* (2013.01); *C12Q 1/6813* (2013.01); *C12Q 1/6837* (2013.01); *C40B 40/06* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 6,194,454 B1 * | 2/2001 | Dow ............................ | 514/522 |
| 7,709,616 B2 | 5/2010 | Bentwich et al. | |
| 2006/0019286 A1 * | 1/2006 | Horvitz ................ | C12Q 1/6809 435/6.11 |
| 2009/0131348 A1 | 5/2009 | Labourier et al. | |
| 2010/0178653 A1 | 7/2010 | Aharonov et al. | |
| 2010/0323357 A1 | 12/2010 | Nana-Sinkam et al. | |

FOREIGN PATENT DOCUMENTS

| | | |
|---|---|---|
| CN | 101307361 | 11/2008 |
| CN | 101384273 A | 3/2009 |
| CN | 101389770 A | 3/2009 |
| CN | 101475984 | 7/2009 |
| EP | 2 133 431 A1 | 12/2009 |
| WO | WO 2007/073737 A1 | 7/2007 |
| WO | WO 2007/081740 A2 | 7/2007 |
| WO | WO 2009/055979 A1 | 5/2009 |

OTHER PUBLICATIONS

Lee et al., "Expression profiling identifies microRNA signature in pancreatic cancer", International Journal of Cancer, vol. 120, p. 1046-1054 (2006).*
Lee et al., "Expression profiling identifies microRNA signature in pancreatic cancer", Int. J. Cancer, vol. 120, p. 1046-1054 (2006).*
Baskerville, S. and Bartel, D.P. 2005 "Microarray profiling of microRNAs reveals frequent coexpression with neighboring miRNAs and host genes" RNA 11: 241-247.
Liu, J. et al. 2009 "Research advancement of microRNA on pancreatic cancer" *Progress in Modern Biomedicine* 9: 4560-4564.
Qin, Y. et al. 2007 "Research advances in the detection of microRNA" *Journal of Medical Postgraduates* 20: 1198-1201.
Chen, X. et al. 2008 "Characterization of microRNAs in serum: a novel class of biomarkers for diagnosis of cancer and other diseases" *Cell Research* 18: 997-1006.
Wang, J. et al. 2009 "MicroRNAs in plasma of pancreatic ductal adenocarcinoma patients as novel blood-based biomarkers of disease" *Cancer Prev Res* 2: 807-813.
Supplemental European Search Report in corresponding European Application No. EP09852423, dated Apr. 26, 2013.
Belair, C. et al. 2009 "Helicobacter pylori and gastric cancer: possible role of microRNAs in this intimate relationship" *Clin Microbiol Infect* 15: 806-812.
Chintharlapalli et al. 2009 "Oncogenic MicroRNA-27a Is A Target For Anticancer Agent Methyl 2-Cyano-3,11-dioxo-18β-olean-1,12-dien-30-oate in Colon Cancer Cells" *Int J Cancer* 125(8): 1965-1974.
Guttilla, I.K. and White B.A. 2009 "Coordinate Regulation of FOXO1 by miR-27a, miR-96, and miR-182 in Breast Cancer Cells" *J Biol Chem* 35: 23204-23216.
Wang, X. et al. 2008 "Aberrant Expression of Oncogenic and Tumor-Suppressive MicroRNAs in Cervical Cancer Is Required for Cancer Cell Growth" *PLos One* 3(7): e2557.

* cited by examiner

*Primary Examiner* — Samuel Woolwine
*Assistant Examiner* — Olayinka Oyeyemi
(74) *Attorney, Agent, or Firm* — Knobbe, Martens, Olson & Bear, LLP

(57) ABSTRACT

The present invention provides microRNAs for assessing the status of pancreatic cancer in a subject, and provides methods, kits, and biochips for detecting said microRNAs.

10 Claims, 6 Drawing Sheets

PANCREATIC CANCER MARKERS, AND DETECTING METHODS, KITS, BIOCHIPS THEREOF

TECHNICAL FIELD

The present invention belongs to the field of biological technology, and relates to the separation of, and the qualitative and quantitative analysis on microRNAs in serum/plasma of human beings, as well as to various clinical indicators of pancreatic cancer. More particularly, the present invention is a method for detecting microRNAs in the serum/plasma of pancreatic cancer patients, which can be used to diagnose pancreatic cancer and chronic pancreatitis in vitro, to evaluate pancreatic cancer stage, to predict pancreatic cancer complication rate, pancreatic cancer relapse rate, and the prognosis of pancreatic cancer, as well as to analyze pharmacological efficacy and therapeutic effect, by analyzing the alteration of microRNAs in serum/plasma.

BACKGROUND OF THE INVENTION

Pancreatic cancer is a type of tumor with high mortality rate (~99.9%, for definitive diagnosed patients). It was estimated that in USA, in 2005, there were 32,180 incidence cases of pancreatic cancer, accounting for 2% of all incidence cancer cases; 31,800 death cases, ranking the $4^{th}$ and $5^{th}$ in the male and female respectively among all causes of deaths related to cancer, taking 5%-6% of all causes of deaths related to cancer. In EU, it was estimated that in 2002, there were 55,100 incidence cases and 59,300 death cases of pancreatic cancer, without definite variations in different genders and races and commonly the prognosis is poor. A statistics for the global oncoming and death of pancreatic cancer patients is shown in Table 1, wherein the term "Incidence Cases" refers to the number of pancreatic cancer cases newly diagnosed in 2002, and the term "Death Cases" refers to the population that were diagnosed as pancreatic cancer by 2002 and died in 2002.

TABLE 1

A statistics of global pancreatic cancer oncoming and death in 2002

| | Male | | Female | |
| --- | --- | --- | --- | --- |
| | Incidence Cases | Death Cases | Incidence Cases | Death Cases |
| USA | 15,900 | 15,000 | 15,800 | 15,400 |
| EU | 28,400 | 29,600 | 26,700 | 29,700 |
| Others | 80,600 | 75,000 | 65,000 | 62,400 |

Therefore, seeking markers for pancreatic cancer and detecting the pancreatic cancer with high accuracy have become an extremely and important precondition of early stage diagnosis and treatment for pancreatic cancer. Although more and more disease markers have been discovered and applied in the clinically general survey and diagnosis of diseases and in therapeutic efficacy monitoring, there are still significant deficiencies in their clinical application. For instance, the tumor markers alpha-fetoprotein (AFP), lactic dehydrogenase (LHD) and carcinoembryonic antigen (CEA) have been widely used in clinic, but the above disease markers are far from meeting the needs for diagnosing cancers at the early stage. The main reasons are as follows: (1) the sensitivity and specificity of the disease markers mentioned above are relatively low, therefore the detection results may yet not be taken as indicators for definite diagnosis of diseases; (2) the diagnosis rate of diseases at an early stage is in positive correlation with the therapeutic efficacy, but any of the disease markers mentioned above satisfies the requirement to diagnosis a disease at an early stage. Take cancer for instance, due to drawbacks including the extremely high specificity among types of differentiated cancers, the relatively low overall sensitivity of tumor bodies, the difficulty of repetitive sampling and the high requirements of sample preservation, and high costs, the application of current existing tumor markers cannot be widely promoted under the current conditions. Meanwhile, some conventional medical methods such as biopsy have inherent deficiencies, such as sampling at wrong sites, insufficiency of tissue and cell sample materials or lack of experience for the technician may all contribute to misdiagnosis. Other techniques like medical imaging that have been widely used in disease examination and diagnosis are rather limited in the qualitative description of disease process. Therefore, it is necessary to find novel disease markers that are sensitive and convenient in application, and capable of overcoming the defects of the currently existing markers.

Micro ribonucleic acids, also called miRNA, are a class of non-coding, single strand, small ribonucleic acid molecules with 19-23 nucleotides in length. They are highly conserved in evolution and closely related to many ordinary biophysical activities of animals, such as ontogenesis, tissue differentiation, apoptosis and energy metabolism, and are closely related to the occurrence and progression of many diseases. Recent research has shown that the expression levels of several miRNAs in chronic lymphocytic leukemia and Burkett lymphoma are down-regulated to varying extents (Lawrie C H, Gal S, Dunlop H M et al. Detection of elevated levels of tumor-associated miRNAs in serum of patients with diffuse large B-cell lymphoma. Br J Haematol 2008; 141:672-675); in the analysis of the expression of miRNAs in human lung cancer and breast cancer tissues, it was observed that the expression levels of some tissue-specific miRNAs is different from those of normal tissues (Garofalo M, Quintavalle C, Di Leva G et al. MicroRNA signatures of TRAIL resistance in human non-small cell lung cancer. Oncogene 2008). There are also researches proving that miRNAs affects the occurrence and progression of angio-cardiopathies including cardiac hypertrophy, heart failure and atherosclerosis, and are closely related to metabolic diseases like diabetes type II (Tryndyak V P, Ross S A, Beland F A, Pogribny I P. Down-regulation of the microRNAs miR-34a, miR-127, and miR-200b in rat liver during hepatocarcinogenesis induced by a methyl-deficient diet. Mol Carcinog. 2008 Oct. 21). All these experimental results suggest that the expression and specific changes of miRNAs are definitely related to the occurrence and progression of diseases.

MiRNAs play a highly important role in the regulation of gene translation subsequent to the transcription, which indicates a relationship between miRNAs and diseases. Firstly, the change of miRNAs may be the cause of the diseases, because the inhibition and promotion factors of diseases may be targets of miRNAs. When the expression of miRNA itself is in disorder, for example when miRNAs that inhibit the disease promotion factors are down-regulated in expression, or miRNAs that inhibit the disease inhibition factors are up-regulated in expression, as a final result, the expression of a series of genes down-stream will be altered, and some gene-pathway will be in disorder, eventually causing diseases. Secondly, the changes of miRNAs are possibly the result of the diseases. This is because when a disease (cancers, for instance) occurs, it may cause loss of chromosome fragments, genetic mutation or instant amplification of chromosome fragments; if the miRNAs are from the affected fragments, the expression levels of these miRNAs will be significantly altered. Therefore, theoretically, miRNAs can be used as a novel class of disease markers; the specific alteration is undoubtedly related to disease occurrence and development. Meanwhile, miRNAs may be used as potential drug target sites; the occurrence and progression of the diseases may be largely relieved by inhibiting the up-regulated miRNAs or over-expressing the down-regulated miRNAs during the disease progression.

Presently, researches on miRNAs as disease markers have been carried out in China. For instance, Chinese patent applications CN100999765A and CN101298630A have disclosed respectively that, in the case of colon cancer, which ranks the 4$^{th}$ of malignant tumor occurrence rate, some miRNAs undergo specific alterations when benign colon polyps deteriorate into malignant tumor. A more sensitive and accurate method for diagnosing early-stage colon cancer has been developed according to the specific alterations of miRNAs. However, the wide clinical application is restrained by the difficulties in tissue sampling.

DISCLOSURE OF THE INVENTION

In order to overcome defects described above, the present inventors have focused on blood that is relatively easier to obtain and even can be collected via routine physical examination. Blood circulates through the body and carries nutrients to and waste materials away from all body tissues and cells. Therefore, blood could reflect the overall physiological and pathological condition of an organism, and the detecting results can function as indicators for human health. It is known that in serum/plasma there are various kinds of proteins such as total protein, albumin and globulin; various lipids such as HDL cholesterol and triglycerides; various carbohydrates; pigments; electrolytes; inorganic salts; and various enzymes such as amylase, alkaline phosphatase, acid phosphatase, cholinesterase and aldolase; moreover, there are also many kinds of signal molecules from tissues and organs throughout the body such as cytokines and hormones. Currently, disease diagnosis is limited to the above-mentioned biochemical indicators in serum/plasma, and there is no report that serum/plasma miRNAs can be used as markers. It is traditionally believed that there is no RNA in serum/plasma. Even if there is any, the RNA will be rapidly degraded by RNase into small molecule segments and hence cannot be detected. However, miRNAs, consisting of 19 to 23 nucleotides, possess specificity and relative stability in structure and hence are very likely to exist in serum/plasma. The preliminary research of the inventor has proven that miRNAs stably exist in the serum/plasma, and various diseases have a matching profile of miRNAs (Chen et al: Characterization of microRNAs in serum: a novel class of markers for diagnosis of cancer and other diseases. Cell Res. 2008 October; 18 (10):997).

In order to seek out pancreatic cancer markers and have them accurately detected, according to current available research results, the inventor has performed research in the following aspects:

(1) research on the specific alterations of serum/plasma miRNAs during the progression of pancreatic cancer;

(2) detecting the alteration of serum/plasma miRNA in pancreatic cancer patients using biochip and sequencing techniques for detecting serum/plasma miRNAs;

(3) The miRNA molecules in serum/plasma which exhibit significantly different expression levels in pancreatic cancer patients, chronic pancreatitis patients and normal subjects are used in serum/plasma miRNAs detection technique, and used \to prepare biochips and diagnosis kits for use in the field of pancreatic cancer diagnosis and the like.

Based on the research on the relationship between the serum/plasma miRNAs and pancreatic cancer, the inventor proposes using certain miRNAs stably existing in serum/plasma as detection markers for pancreatic cancer. The inventor further establishes a method for in vitro detecting the miRNAs stably existing in serum/plasma. By detecting the specific alterations of the certain miRNAs, a person skilled in the art is capable of diagnosing pancreatic cancer at an early stage, identificating and diagnosing of the chronic pancreatitis, identificating diseases and monitoring disease process, determining the relapse and prognosis of the disease, and predicting the complication occurrence. A person skilled in the art is further carry out researches on determining drug efficacy, medication guidance and individualized treatment, screening for the active ingredients from herbs, and on the population taxonomy.

Therefore, the present invention aims at providing a pancreatic cancer marker.

The present invention further aims at providing a combination of probes for detecting the pancreatic cancer markers.

The present invention further aims at providing a use of the above described pancreatic cancer marker, which includes preparing corresponding kits and biochips.

The present invention further aims at providing a method for detecting the pancreatic cancer marker described above.

The aims of the present invention are achieved by the technical solutions as follows.

In one aspect, the present invention provides a pancreatic cancer marker, which includes one or more than one mature miRNAs (mature microRNAs) selected from the following group, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 mature miRNAs selected from the following group, wherein said mature miRNAs stably exists in human serum/plasma and maybe detected therefrom, and the group of mature microRNAs comprises: miR-27a, miR-27b, miR-29a, miR-29c, miR-30a, miR-30d, miR-33a, miR-92a, miR-100, miR-101, miR-103, miR-125b, miR-130b, miR-140-3p, miR-148a, miR-192, miR-199a, miR-199a-3p, miR-222, miR-210, miR-215, miR-223, miR-320, miR-361-5p, miR-378, miR-411, miR-483-5p, miR-20a, miR-21, miR-24, miR-25, miR-26a, miR-99, miR-122, miR-185 and miR-191, in which miR-320 includes, e.g. miR-320a and miR-320b.

Preferably, the marker can be one or more than one mature miRNAs selected from the following group, such as 2, 3, 4, 5, 6 or 7 mature miRNAs selected from the following group, wherein said mature miRNAs stably exists in human serum/plasma and maybe detected therefrom, and the group of mature microRNAs comprises: miR-20a, miR-21, miR-24, miR-25, miR-99, miR-185 and miR-191.

The present invention also provides a pancreatic cancer marker, which includes two or more than two mature miRNAs selected from the following group, such as 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 mature miRNAs selected from the following group, wherein said mature miRNAs stably exists in human serum/plasma and maybe detected therefrom, and the group of mature microRNAs comprises: miR-27a, miR-27b, miR-29a, miR-29c, miR-30a, miR-30d, miR-33a, miR-92a, miR-100, miR-101, miR-103, miR-125b, miR-130b, miR-140-3p, miR-148a, miR-192, miR-199a, miR-199a-3p, miR-222, miR-210, miR-215, miR-223, miR-320, miR-361-5p, miR-378, miR-411, miR-483-5p, miR-20a, miR-21, miR-24, miR-25, miR-26a, miR-99, miR-122, miR-185 and miR-191.

Preferably, the marker includes two or more than two mature miRNAs selected from the following group, such as 3, 4, 5, 6 or 7 mature miRNAs selected from the following group, wherein said mature miRNAs stably exists in human serum/plasma and maybe detected therefrom, and the group of mature microRNAs comprises: miR-20a, miR-21, miR-24, miR-25, miR-99, miR-185 and miR-191.

The above serum/plasma may originate from living bodies, tissues, organs and/or corpses of human beings.

In another aspect, the present invention provides a method for detecting the above marker, and the method comprises one or more selected from Reverse Transcription-Polymerase Chain Reaction (RT-PCR), Real-time Fluorescent Quantitative Polymerase Chain Reaction (Real Time-PCR), Northern blotting, RNase protection, Solexa sequencing technology and the biochip method.

Preferably, the method is a RT-PCT method, for example a RT-PCR method comprising the following steps:

(1) extracting total RNA from the serum/plasma of a subject, and obtaining cDNA samples by RNA reverse transcription reaction; or, collecting the serum/plasma samples from a subject and preparing cDNA samples by reverse transcription reaction with the serum/plasma as a buffer solution;

(2) carrying out PCR reaction with primers designed based on the miRNAs;

(3) performing the Agarose Gel Electrophoresis with the PCR products;

(4) observing the results under the ultra-violet lamp after EB staining.

Or preferably, the method is a Real-time PCR method, such as a RT-PCR method comprising the following steps:

(1) extracting total RNA from the serum/plasma of a subject, and obtaining cDNA products by the RNA reverse transcription reaction; or, collecting the serum/plasma samples from a subject, and preparing the cDNA samples by the reverse transcription reaction with the serum/plasma as a buffer solution;

(2) designing primers based on the miRNAs;

(3) performing PCR reaction after adding fluorescent probes;

(4) detecting alteration in the amount of miRNAs in the serum/plasma samples compared with that of miRNAs in the normal serum/plasma.

To be specific, the method according to the present invention for detecting the above 36 miRNAs in the serum/plasma of a subject may further be used to evaluate the conditions of a pancreatic cancer patient. The method for detecting the 36 miRNAs stably existing and detectable in serum/plasma of human beings comprises one or more selected from Reverse Transcription-Polymerase Chain Reaction (RT-PCR), Fluorescent Quantitative Polymerase Chain Reaction (Real-time PCR), Northern blotting, RNase protection, Solexa sequencing technology and the biochip method.

The RT-PCR method includes the following steps: (1) collecting the serum/plasma samples, particularly extracting total RNA from human serum/plasma with an reagent such as Trizol reagent, and preparing the cDNA samples by RNA reverse transcription reaction; or, collecting the serum/plasma samples from a subject, and preparing cDNA samples by reverse transcription reaction with the serum/plasma as a buffer solution; (2) performing the PCR reaction with the primers designed based on the miRNAs; (3) performing Agarose Gel Electrophoresis with the PCR products; (4) observing the results under the ultra-violet lamp after EB staining, and taking photos.

The Real-time PCR method includes the following steps: (1) collecting the serum/plasma samples; particularly, extracting total RNA from the serum/plasma with a reagent such as Trizol reagent, and obtaining cDNA samples by RNA reverse transcription reaction; or, preparing cDNA samples by reverse transcription reaction with the serum/plasma as a buffer solution; (2) designing primers based on the miRNAs; (3) adding fluorescent probes, such as the EVA GREEN, and performing the PCR reaction; (4) analyzing the data and comparing the results, specifically, detecting the amount alteration of the miRNAs in the serum/plasma samples comparing with that of the miRNAs in normal serum/plasma.

The Northern blotting method includes the following steps: (1) collecting serum/plasma samples; (2) extracting total RNA from the serum/plasma samples with Trizol reagent; (3) performing denaturing PAGE electrophoresis and membrane transfer procedures; (4) preparing isotope labeling probes for the miRNAs; (5) performing the membrane hybridizing reaction; (6) detecting the isotope signals, e.g., the results is obtained in P-screen scanning.

The RNase protection assay includes the following steps: (1) preparing probes as anti-sense RNAs, and performing isotope labeling and purification; (2) collecting serum/plasma samples and extracting the RNAs; (3) dissolving the extracted RNAs in a hybridizing buffer solution, placing the anti-sense RNA probes and performing hybridizing reaction; (4) adding RNase digestion solution and performing the reaction; (5) performing the electrophoresis and autoradiography; (6) analyzing the results.

The method of Solexa sequencing technology includes the following steps: (1) collecting serum/plasma samples; (2) extracting total RNA from the serum/plasma samples with Trizol reagent; (3) performing PAGE electrophoresis to recover 17-27 nt RNA molecules; (4) connecting the adaptor prime enzymes to the 3' and 5' end of the RNA molecules; (5) perform RT-PCR reaction and then sequencing the products; (6) analyzing and processing the data.

The biochip method includes the following steps: (1) preparing a lattice of all the human mature miRNAs which is more than 500, and prepare biochips thereof; (2) collecting serum/plasma samples; (3) extracting total RNA from the serum/plasma samples; (4) separating the miRNAs by ways of column separation; (5) fluorescent labeling the miRNAs with T4 RNA ligase; (6) performing hybridizing reaction on the biochips; (7) determining and analyzing the data.

In the present invention, by using methods above like RT-PCR, Real-time PCR, Northern blotting, RNase protection assay, Solexa sequencing technology and the biochip method, and the like, the alteration tendency and the alteration in the content of miRNAs in the serum/plasma of pancreatic cancer patients, and the relationship between the miRNAs and the pancreatic cancer studied. Particularly, the alterations of miR-27a, miR-27b, miR-29a, miR-29c, miR-30a, miR-30d, miR-33a, miR-92a, miR-100, miR-101, miR-103, miR-125b, miR-130b, miR-140-3p, miR-148a, miR-192, miR-199a, miR-199a-3p, miR-222, miR-210, miR-215, miR-223, miR-320, miR-361-5p, miR-378, miR-411, miR-483-5p, miR-20a, miR-21, miR-24, miR-25, miR-26a, miR-99, miR-122, miR-185, miR-191 are determined in pancreatic cancer. Biochips of the serum/plasma miRNAs are prepared to detect the alteration of the serum/plasma miRNAs in different diseases, whilst Solexa sequencing is performed on the serum/plasma miRNAs in different diseases.

The serum/plasma used in the method originates from living bodies, tissues, organs and/or corpses of subjects.

The present invention also provides a method for predicting, diagnosing identifying and/or evaluating pancreatic cancer; the method includes detecting the marker mentioned above. Preferably, the method includes detecting the above-mentioned marker using the aforesaid detecting methods.

The present invention provides a use of the non-small cell lung cancer marker in the preparation of reagents or tools for the prediction, diagnosis, identifying and/or evaluation of pancreatic cancer.

The present invention also provides a combination of miRNA targeting probes used for detecting the pancreatic cancer marker, that is, a combination of miRNA targeting probes for detecting, diagnosing and/or evaluating pancreatic cancer. The aforesaid combination of probes comprises one or more probes selected from probes defined by the following nucleotide sequences, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 probes selected from probes defined by the following nucleotide sequences. Preferably, the aforesaid combination of probes comprises two or more than two of the probes selected from probes defined by the following nucleotide sequences, such as 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 probes selected from probes defined by the following nucleotide sequences:

| miRNA | Corresponding probe sequence | Sequence serial |
|---|---|---|
| miR-27a | GCGGAACTTAGCCACTGTGAA | SEQ ID NO. 1 |
| miR-27b | GCAGAACTTAGCCACTGTGAA | SEQ ID NO. 2 |
| miR-29a | AACCGATTTCAGATGGTGCTA | SEQ ID NO. 3 |
| miR-29c | ACCGATTTCAAATGGTGCTA | SEQ ID NO. 4 |
| miR-30a | CTTCCAGTCGAGGATGTTTACA | SEQ ID NO. 5 |
| miR-30d | CTTCCAGTCGGGGATGTTTACA | SEQ ID NO. 6 |
| miR-33a | CAATGCAACTACAATGCAC | SEQ ID NO. 7 |
| miR-92a | CAGGCCGGGACAAGTGCAATA | SEQ ID NO. 8 |
| miR-100 | CACAAGTTCGGATCTACGGGTT | SEQ ID NO. 9 |
| miR-101 | CTTCAGTTATCACAGTACTGTA | SEQ ID NO. 10 |
| miR-103 | TCATAGCCCTGTACAATGCTGCT | SEQ ID NO. 11 |
| miR-125b | TCACAAGTTAGGGTCTCAGGGA | SEQ ID NO. 12 |
| miR-130b | ATGCCCTTTCATCATTGCACTG | SEQ ID NO. 13 |
| miR-140-3p | CTACCATAGGGTAAAACCACT | SEQ ID NO. 14 |
| miR-148a | ACAAAGTTCTGTAGTGCACTGA | SEQ ID NO. 15 |
| miR-192 | GGCTGTCAATTCATAGGTCAG | SEQ ID NO. 16 |
| miR-199a | GAACAGGTAGTCTGAACACTGGG | SEQ ID NO. 17 |
| miR-199a-3p | AACCAATGTGCAGACTACTGTA | SEQ ID NO. 18 |

-continued

| miRNA | Corresponding probe sequence | Sequence serial |
|---|---|---|
| miR-222 | GAGACCCAGTAGCCAGATGTAGCT | SEQ ID NO. 19 |
| miR-210 | TCAGCCGCTGTCACACGCACAG | SEQ ID NO. 20 |
| miR-215 | GTCTGTCAATTCATAGGTCAT | SEQ ID NO. 21 |
| miR-223 | GGGGTATTTGACAAACTGACA | SEQ ID NO. 22 |
| miR-320 | TTCGCCCTCTCAACCCAGCTTTT | SEQ ID NO. 23 |
| miR-361-5p | GTACCCCTGGAGATTCTGATAA | SEQ ID NO. 24 |
| miR-378 | ACACAGGACCTGGAGTCAGGAG | SEQ ID NO. 25 |
| miR-411 | CGTACGCTATACGGTCTACTA | SEQ ID NO. 26 |
| miR-483-5p | AGAAGACGGGAGGAGAGGAGTGA | SEQ ID NO. 27 |
| miR-20a | CTACCTGCACTATAAGCACTTTA | SEQ ID NO. 28 |
| miR-21 | TCAACATCAGTCTGATAAGCTA | SEQ ID NO. 29 |
| miR-24 | CTGTTCCTGCTGAACTGAGCCA | SEQ ID NO. 30 |
| miR-25 | TCAGACCGAGACAAGTGCAATG | SEQ ID NO. 31 |
| miR-26a | GCCTATCCTGGATTACTTGAA | SEQ ID NO. 32 |
| miR-99 | CACAAGATCGGATCTACGGGTT | SEQ ID NO. 33 |
| miR-122 | ACAAACACCATTGTCACACTCCA | SEQ ID NO. 34 |
| miR-185 | GAACTGCCTTTCTCTCCA | SEQ ID NO. 35 |
| miR-191 | AGCTGCTTTTGGGATTCCGTTG | SEQ ID NO. 36 |

The present invention also provides a combination of miRNA targeting probes for detecting pancreatic cancer marker, that is, a combination of miRNA targeting probes for the prediction, diagnosis and/or evaluation of pancreatic cancer. The aforesaid combination of probes includes one or more than one probes selected from the probes defined by the following nucleotide sequences, such as 2, 3, 4, 5, 6 or 7 probes selected form the probes defined by the following nucleotide sequences:

| miRNA | Corresponding probe sequence | Sequence Serial |
|---|---|---|
| miR-20a | CTACCTGCACTATAAGCACTTTA | SEQ ID NO. 28 |
| miR-21 | TCAACATCAGTCTGATAAGCTA | SEQ ID NO. 29 |
| miR-24 | CTGTTCCTGCTGAACTGAGCCA | SEQ ID NO. 30 |
| miR-25 | TCAGACCGAGACAAGTGCAATG | SEQ ID NO. 31 |
| miR-99 | CACAAGATCGGATCTACGGGTT | SEQ ID NO. 33 |
| miR-185 | GAACTGCCTTTCTCTCCA | SEQ ID NO. 35 |
| miR-191 | AGCTGCTTTTGGGATTCCGTTG | SEQ ID NO. 36 |

The present invention provides a kit for detecting the pancreatic cancer marker, that is, a kit for the prediction, diagnosis, identifying and/or evaluation of pancreatic cancer. The aforesaid kit comprises a tool for detecting the marker mentioned above. Preferably, the tool comprises the combination of miRNA targeting probes for detecting the pancreatic cancer marker; more preferably, the aforesaid tool further comprises polymerase and DNA. The kit for diagnosis of pancreatic cancer is prepared by collecting the primers or corresponding probes of miRNAs which show specific alterations when screened with pancreatic cancer into the PCR kit (RT-PCR or Real-time PCR).

The present invention also provides a biochip for detecting the pancreatic cancer marker, that is, a biochip for the prediction, diagnosing identifying and/or evaluating pancreatic cancer, which comprises a component for detecting the marker mentioned above. Preferably, the component comprises the combination of miRNA targeting probes for detecting the pancreatic cancer marker. [till] The biochip for detecting miRNAs in serum/plasma specified for pancreatic cancer can be prepared by dotting the reverse compliment sequences of the selected miRNAs as probes on the chip with variations specific to pancreatic cancer.

More specifically, in any one of the combinations, methods, kits or biochips containing 1 to 36 miRNAs selected from the miRNA markers above, the aforesaid evaluating of pancreatic cancer may refer to evaluating pancreatic cancer after the subjects have been given drug candidates (drugs for pancreatic cancer treatment), particularly for the purpose of screening the efficacy of the drug candidates in the prevention and/or treatment of the pancreatic cancer. Further, evaluating the condition of pancreatic cancer in the subjects may refer to diagnosing and/or identifying the disease of the subjects. Still further, evaluating the condition of pancreatic cancer in the subjects may refer to evaluating the treatment efficiency in the disease of the subjects. Evaluating the condition of pancreatic cancer in the subjects may also refer to predicting the oncoming of the pancreatic cancer of the subjects, wherein the oncoming of pancreatic cancer particularly refers to the occurrence of pancreatic cancer complication and/or relapse of pancreatic cancer. The possible causes of pancreatic cancer include chronic pancreatitis; pathological studies also reveal the gradual progression from normal pancreatic tissues to hyperplasia, and then to pancreatic cancer. Patients with early pancreatitis, such as hereditary pancreatitis and tropical pancreatitis may have higher risk to develop pancreatic cancer and therefore extended duration of chronic inflammation is a major cause of oncogenesis. A certain proportion of misdiagnosis exists in pancreatic cancer with chronic pancreatitis history and chronic pancreatitis. Therefore, it is quite important to identify and diagnose the pancreatic cancer and chronic pancreatitis in vitro.

Presently, the traditional techniques of biochemistry and molecular biology for clinical diagnosis are complex and crude. In the recent years, new technologies have been developed which may be useful in disease diagnosis, including the gene chip and protein (anti-body) chip technique and the like. The mRNA level variation detected by the gene chip cannot completely reflect the actual variation of protein level, because the bio-activity of proteins is closely related to post translational modifications such as glycosylation and phosphorylation. Also, for the detection of many diseases, the gene chip technique cannot detect the marker in body fluid and blood. Meanwhile, the protein (anti-body) chip technique and the proteomics technique are also limited. There are tens of thousands of proteins and polypeptide segments in human body, especially in the serum/plasma, which are widely distributed in concentration. Few proteins have been definitely reported, and much fewer are quantified. It is a tremendous task to seek out the proteins closely related to certain diseases amongst the numerous protein groups and to understand their functions during the tissue pathological process. Also, the development of anti-body chip technique is restrained by the lack of complete anti-body resources. In the biochip and diagnosis kit based on serum/plasma miRNA, the unique characteristics of serum/plasma miRNAs is combined with conventional molecular biological detection technologies. The biochips and kit may analyze the composition of the miRNAs existing in the serum/plasma of pancreatic cancer patients in high-throughput, thereby shows good clinical applicability. Since the physiological variations in the condition of the organs and tissues cause variations of miRNA composition in serum/plasma, miRNAs in serum/plasma can be used as the "fingerprint" of disease to achieve the early stage diagnosis of pancreatic cancer.

To summarize, the present invention provides the following advantages:

(1) The method using screened miRNAs in serum/plasma as the pancreatic cancer markers possesses advantages including wide detection coverage, high sensitivity, low cost, convenient sampling and sample preservation (serum/plasma can be preserved at −20° C.), etc. The method can be widely applied in the tasks such as general disease survey and the like, and becomes an effective method for early diagnosis.

(2) Having serum/plasma miRNAs as novel disease markers would solve the problems of low specificity and low sensitivity with other signal marker detection caused by unavoidable individual differences, and remarkably increase the clinical detection rate of diseases and achieve early diagnosis and treatment.

(3) The advantage of the serum/plasma miRNA detection technique is that, by detecting a class of disease related markers, it can avoid influence from individual differences of patients (including age, gender, race, diet and environment conditions, and etc.), which is one of the major problems that single marker detection techniques cannot solve.

In summary, the present invention can be further applied in the diagnosis of pancreatic cancer at early stage, and the novel markers of pancreatic cancer in serum/plasma not only provide the foundation for fully understanding the mechanism of pancreatic cancer at the molecular level, but also accelerate the advances in clinical diagnosis and treatment. It is believed that, with the advantages of the serum/plasma miRNAs, the serum/plasma miRNAs diagnosis technique for severe diseases including cancer shall become part of general physical examination; as the genetic treatment related to miRNAs is being widely applied, conquering these diseases shall be no longer a dream.

BRIEF DESCRIPTION OF THE DRAWINGS

Drawings are referred to illustrate the examples of the present invention, wherein:

In FIG. 1 and FIG. 2, U6 is a snRNA with a molecular weight of 100 bp, serving as an internal reference molecule in miRNA experiments. The other 12 miRNAs are: miR-181a (181a), miR-181b (181b), miR-223 (223), miR-142-3p (142-3p), miR-142-5p (142-5p) and miR-150 (150) with blood cell specificity; miR-1 (1), miR-133a (133a), miR-206 (206) from cardiac muscles and skeletal muscles; miR-9 (9), miR-124a (124a) from brain tissues; and miR-122a (122a) from liver.

PREFERRED EMBODIMENTS OF THE INVENTION

It shall be understood that the embodiments described specifically herein are illustrated by examples, which are not intended to limit the scope of the invention. The major features of the present invention can be applied in various embodiments without departing from the scope of the invention. It will be recognized by persons skilled in the art that the conventional experiments and many equivalents thereof may be applied in certain steps described above. Such equivalents are believed to be within the scope of the invention and covered by the appended claims.

Example 1

RT-PCR Experiments of miRNAs in Serum/Plasma

By using the RT-PCR assay, it is found and proved that various miRNAs exist stably in serum/plasma of both human beings and other animals, and that their expression levels are considerably high. The specific steps are as follows:

(1) collecting serum/plasma of mice, rats, normal human subjects and patients;

(2) preparing cDNA samples. This operation has two options: one is to directly conduct the reverse transcription reaction using 10 μl of serum/plasma; the other one is to first extract total RNA from serum/plasma with Trizol reagent (Invitrogen Co.) (typically about 10 μg of RNA can be enriched from 10 μl of serum/plasma), and then to obtain cDNA by the RNA reverse transcription reaction. The reaction system of reverse transcription comprises 4 μl of 5×AMV buffer, 2 μl 10 mM of each dNTP mixture (Takara Co.), 0.5 μl of RNase Inhibitor (Takara Co.), 2 μl of AMV (Takara Co.) and 1.5 μl of gene specific reverse primer mixtures. The reaction steps successively include 15 minutes of incubation at 16° C., 1 hour of reaction at 42° C. and 5 minutes of incubation at 85° C.

(3) PCR and Electrophoresis observation. The cDNA is diluted in the ratio of 1/50. 1 μl of diluted cDNA is added 0.3 μl of Taq polymerase (Takara Co.), 0.2 μl 10 μM of forward primer, 0.2 μl 10 μM of common reverse primer, 1.2 μl 25 mM of $MgCl_2$, 1.6 μl 2.5 mM of each dNTP mixture (Takara Co.), 2 μl of 10×PCR buffer, 13.5 μl of $H_2O$, and the PCR reaction is conducted in a 20 μl system. The PCR reaction is performed under the following conditions: one cycle at 95° C. for 5 mins followed by 40 cycles at 95° C. for 15 seconds and 60° C. for 1 minute. 100 of PCR product is subjected to 3% Agarose Gel Electrophoresis, which is observed under the ultra violet lamp after EB staining.

Figure 1:
FIG. 1 shows the RT-PCR results of part of the miRNAs directly detected in the serum of normal human subjects.

The detailed experimental results are shown in FIG. 1, which shows the experimental results of RT-PCR directly conducted on the serum of normal human subjects. Over 500 mature miRNAs of human beings are selected for conducting the RT-PCR reaction, and 12 miRNAs of which are shown in FIG. 1 and are respectively, miRNAs miR-181a, miR-181b, miR-223, miR-142-3p, miR-142-5p, miR-150 with blood cell specificity; miRNAs miR-1, miR-133a, miR-206 from cardiac muscles and skeletal muscles; miRNAs miR-9 and miR-124a from brain tissues; and miRNA miR-122a from liver. It can be seen from the results that all miRNAs originated from the four tissues mentioned above are detectable in blood. On the other hand, not all total 500 mature miRNAs have high expression levels in the serum/plasma, and some are present only in extreme trace amount, even cannot be detected.

Figure 2:
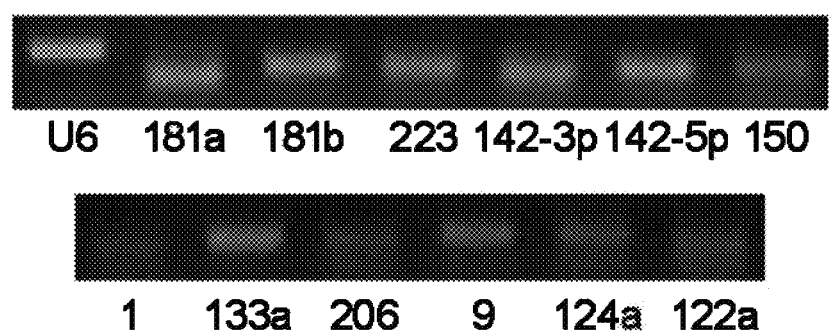
FIG. 2 shows the RT-PCR results of the miRNAs in the RNAs extracted from the serum of normal human subjects.
Figure 3:
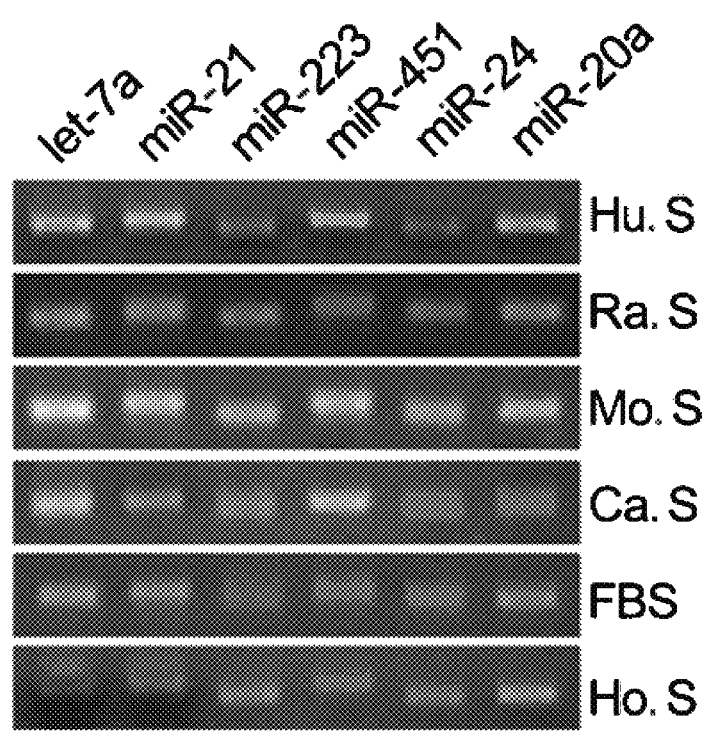
FIG. 3 shows the RT-PCR results of part of the miRNAs directly detected in the serum of mice, rat, fetal bovine, calf, and horse respectively.

To further verify that these miRNAs exist stably in serum/plasma, RNA is firstly extracted from the serum of normal human subjects, and then over 500 mature human miRNAs are selected for PCR experiment, the results of which are shown in FIG. 2. The results in FIG. 2 are quite consistent with those of FIG. 1, and the PCR products are simplex, which indicates that both assays can detect the expression and abundance of the miRNAs in human serum/plasma, and proves that tissue-originated miRNAs exist stably in human serum/plasma. In addition, the same methods are used to detect the expression and abundance of over 500 miRNAs in the serum/plasma of mouse, rat, fetal bovine, calf and horse; it is also found that there is stable expression of tissue-specific miRNAs in serum/plasma of mouse, rat, fetal bovine, calf and horse (see FIG. 3 for the results).

Example 2

Real-Time PCR Experiments of miRNAs in Serum/Plasma

Quantitative PCR experiments on serum/plasma miRNAs are conducted in order to study the specific variations of these miRNAs during the progression of pancreatic cancer. The principles and steps of the quantitative experiment are the same as those of RT-PCR, except that the fluorescent dye EVA GREEN is added during PCR. An ABI Prism 7300 fluorescent quantitative PCR instrument is used to conduct the PCR reaction under the following conditions: one cycle at 95° C. for 5 mins followed by 40 cycles at 95° C. for 15 seconds and 60° C. for 1 minute. The data processing method is the ΔΔCT method, wherein CT is the number of cycles when the reaction reaches the threshold. The expression level of each miRNA relative to an internal standard reference can be expressed by the equation of 2-ΔCT, wherein $\Delta CT = CT_{sample} - CT_{internal\ reference}$. The reverse transcription reactions are directly conducted on serum/plasma samples of a patient and a normal human subject, and the quantities of miRNAs contained in each sample of serum/plasma are compared by the quantitative PCR reactions.

The serum samples of aplastic anemia, breast cancer, osteosarcoma, CNS (Central Nervous System) lymphoma and diabetes patients are selected, and over 500 mature miRNAs of human beings were used to conduct PCR reaction experiments. MiRNAs mR-181a, miR-181b, miR-223, miR-142-3p, miR-142-5p, miR-150 with blood cell specificity; miRNAs miR-1, miR-133a, miR-206 from cardiac muscles and skeletal muscles; miRNAs miR-9, miR-124a from brain tissues; and miRNA miR-122a from liver described above are used to conduct the PCR experiment in the serum of a normal subject and a patient. The ratio of the miRNA content in serum between the aplastic anemia, breast cancer, osteosarcoma, CNS (Central Nervous System)

lymphoma, diabetes patients and the normal subject are respectively up or down-regulated, and the extent of variation in content of the miRNAs from the same tissue source differs in patients with different diseases, indicating that there is specific variation of miRNA expression in the serum/plasma of patients with different diseases. Therefore, miRNAs can function as a novel type of marker for disease diagnosis.

Example 3

Biochip Utilizing Serum/Plasma miRNAs for the Diagnosis of Pancreatic Cancer

The operation steps of the biochip are as follows:

(1) extracting total RNA from serum/plasma, and measuring the mass of total RNA by formaldehyde denaturing gel electrophoresis;

(2) separating miRNAs: miRNAs are separated with Ambion's miRNA Isolation Kit (Cat #. 1560) from 50-100 µg of total RNA;

(3) conducting fluorescent labeling on miRNA samples: the miRNA samples are fluorescent labeled using the T4 RNA ligase labeling method, and then are precipitated with anhydrous ethanol, dried and then used for biochip hybridization;

(4) hybridizing and cleaning: RNAs are dissolved in 160 hybridizing solution (15% formamide; 0.2% SDS; 3×SSC; 50×Denhardt's solution), hybridized overnight under 42° C. After the hybridization, the RNAs are washed for 4 mins in a solution of 0.2% SDS, 2×SSC around 42° C., and for 4 mins in the solution of 0.2% SDS under room temperature, and then the biochips are spun until dry for scanning;

(5) scanning biochips: the chips are scanned with a LuxScan 10K/A double channel laser scanner;

(6) obtaining and analyzing data: the chip images are analyzed with a LuxScan3.0 image analysis software so that the image signals are transferred into digital signals. Finally, the differential expressed genes are selected by SAM analysis.

The probes for the significantly differentially-expressed serum/plasma miRNAs in pancreatic cancer serum samples compared to normal subject serum samples, which are double verified with the quantitative PCR technique and the biochip method, are applied in the preparation of biochips with the same method mentioned above. Compared to conventional biochips, there is no significant improvement in preparing procedure and operation procedures; however, such biochips simplify the probe library, resulting in reduced cost and time for the preparation of the biochips and thus facilities preparation. Meanwhile, the pertinence and practicality of the biochips are improved. When the biochips are used in practical, they may be used to detect diseases in early stage and assist the diagnosis and treatment using only the serum/plasma of the tissues and without any other tissues thereof.

Example 4

MiRNA Kit for the Diagnosis and Prediction of Pancreatic Cancer

The preparation and operation procedures of the miRNA kit for the diagnosis of pancreatic cancer, prediction of complication occurrence and cancer relapse, evaluation of treatment efficacy, selection of the active elements from herbs, and evaluation of drug efficacy are based on the quantitative and semi-quantitative PCR and the biochip method.

First, the miRNAs with more than one copy in normal serum/plasma are determined by sequencing or PCR technique. Then, the serum/plasma miRNAs with significantly different expression levels and obvious variations between the pancreatic cancer progression samples and the subjects in normal physiological status are screened by quantitative PCR technique and biochip method, and they are used as indicators for pancreatic cancer occurrence and disease progression degree. Finally, 36 serum/plasma miRNAs are obtained in the screen for use as indicators for each diseases, which form the most simplified probe library. The aforesaid kit comprises a series of serum/plasma miRNA primers, Taq polymerase and dNTP, etc.

In this example, all the detection samples are from patients diagnosed as pancreatic cancer, chronic pancreatitis and normal subjects with the same age and gender as the patients (the control group).

First, the miRNAs with more than one copy in the normal serum/plasma are determined by Solexa sequencing technique. By detecting the variations of the serum/plasma miRNAs, 63 miRNAs showing alterations in serum samples of pancreatic cancer patients compared with normal human subjects (the control group) are obtained in the screen, of which 44 miRNAs are up-regulated, and 19 miRNAs are down-regulated. For more detailed results, see Table 2.

TABLE 2

Sequencing results which reveal the differentially-expressed miRNAs in the serum samples of pancreatic cancer patients and control serum samples

| Up-regulated miRNAs | | | Down-regulated miRNAs | | |
|---|---|---|---|---|---|
| | miRNA copy numbers | | | miRNA copy numbers | |
| Serial miRNA | control sample | NSCLC samples | Serial miRNA | control sample | NSCLC samples |
| 1 let-7a | 649 | 1566 | 1 miR-1 | 229 | 15 |
| 2 let-7b | 381 | 2454 | 2 miR-107 | 35 | 3 |
| 3 let-7c | 202 | 3808 | 3 miR-125b | 21 | 0 |
| 4 let-7d | 119 | 875 | 4 miR-139-3p | 68 | 0 |
| 5 let-7f | 126 | 2092 | 5 miR-146b-5p | 26 | 5 |
| 6 let-7g | 33 | 458 | 6 miR-150 | 151 | 0 |
| 7 let-7i | 19 | 962 | 7 miR-197 | 49 | 0 |
| 8 miR-100 | 11 | 624 | 8 miR-206 | 203 | 0 |
| 9 miR-101 | 5 | 844 | 9 miR-22 | 481 | 0 |
| 10 miR-103 | 55 | 476 | 10 miR-221 | 41 | 0 |
| 11 miR-122 | 1438 | 31232 | 11 miR-222 | 30 | 2 |
| 12 miR-125a-5p | 19 | 134 | 12 miR-28-3p | 38 | 0 |
| 13 miR-128 | 16 | 59 | 13 miR-339-5p | 78 | 0 |
| 14 miR-140-3p | 48 | 266 | 14 miR-423-5p | 585 | 152 |
| 15 miR-148a | 1 | 193 | 15 miR-484 | 53 | 0 |
| 16 miR-185 | 362 | 873 | 16 miR-486-3p | 24 | 0 |
| 17 miR-185* | 0 | 135 | 17 miR-486-5p | 1640 | 9 |
| 18 miR-191 | 29 | 846 | 18 miR-532-3p | 26 | 0 |
| 19 miR-192 | 14 | 14894 | 19 miR-584 | 22 | 0 |
| 20 miR-193b* | 0 | 185 | | | |
| 21 miR-199a-3p | 16 | 1604 | | | |
| 22 miR-20a | 0 | 245 | | | |
| 23 miR-21 | 38 | 1571 | | | |
| 24 miR-210 | 2 | 81 | | | |
| 25 miR-215 | 0 | 368 | | | |
| 26 miR-24 | 21 | 172 | | | |
| 27 miR-25 | 21 | 237 | | | |
| 28 miR-26a | 14 | 227 | | | |
| 29 miR-27a | 7 | 240 | | | |
| 30 miR-27b | 4 | 462 | | | |

TABLE 2-continued

Sequencing results which reveal the differentially-expressed miRNAs in the serum samples of pancreatic cancer patients and control serum samples Down-regulated miRNAs

| | Up-regulated miRNAs | | | miRNA copy numbers | |
|---|---|---|---|---|---|
| Serial | miRNA | control sample | NSCLC samples | Serial miRNA | control sample | NSCLC samples |

| Serial | miRNA | control sample | NSCLC samples |
|---|---|---|---|
| 31 | miR-29a | 47 | 1800 |
| 32 | miR-29c | 7 | 232 |
| 33 | miR-30a | 4 | 1679 |
| 34 | miR-30d | 187 | 926 |
| 35 | miR-320a | 361 | 1193 |
| 36 | miR-320b | 9 | 188 |
| 37 | miR-361-5p | 1 | 322 |
| 38 | miR-378 | 26 | 382 |
| 39 | miR-451 | 14 | 34 |
| 40 | miR-483-5p | 70 | 1130 |
| 41 | miR-92a | 115 | 331 |
| 42 | miR-95 | 0 | 99 |
| 43 | miR-99 | 40 | 413 |
| 44 | miR-532-5p | 0 | 377 |

A class of serum/plasma miRNAs is obtained in the screening process using qRT-PCR and the biochip method, wherein the miRNAs obtained show significant alteration between patients with a disease and patients under normal physiological condition. As shown in Table 2, miRNAs with the alteration ratio larger than 5 and the copy number lager than 10 are permitted. Then considering the results obtained in prior studies, 36 miRNAs are selected as lab-measuring indicators which are then used as indicators for predicting whether pancreatic cancer is onset, or for diagnosing the progression of the disease. Please see Table 3 for details.

TABLE 3

36 miRNAs Selected

| Serial | miRNA | Average alteration-fold | P value (t-test) |
|---|---|---|---|
| 1 | miR-27a | 1.2960753 | 0.008085 |
| 2 | miR-27b | 1.07 | 0.7567261 |
| 3 | miR-29a | 1.1431785 | 0.3623874 |
| 4 | miR-29c | 1.320792 | 0.1492103 |
| 5 | miR-30a | 1.4954582 | 0.0731187 |
| 6 | miR-30d | 0.8956235 | 0.5688125 |
| 7 | miR-33a | 1.04576 | 0.93872 |
| 8 | miR-92a | 1.2414502 | 0.3052584 |
| 9 | miR-100 | 1.0234521 | 0.9108538 |
| 10 | miR-101 | 1.079218 | 0.7229841 |
| 11 | miR-103 | 1.0661197 | 0.7972754 |
| 12 | miR-125b | 1.3597159 | 0.2975648 |
| 13 | miR-130b | 1.058926 | 0.817821 |
| 14 | miR-140-3p | 1.042287 | 0.7037122 |
| 15 | miR-148a | 1.0481299 | 0.8971156 |
| 16 | miR-192 | 1.3246894 | 0.2644458 |
| 17 | miR-199a | 1.5767 | 0.0386 |
| 18 | miR-199a-3p | 1.363585 | 0.2153148 |
| 19 | miR-222 | 0.9764046 | 0.8690469 |
| 20 | miR-210 | 1.3872444 | 0.3868377 |
| 21 | miR-215 | 0.9732919 | 0.9444299 |
| 22 | miR-223 | 1.08 | 0.613 |
| 23 | miR-320a | 1.493328 | 0.0640379 |
| 24 | miR-361-5p | 1.5194114 | 0.3374292 |
| 25 | miR-378 | 1.2340253 | 0.4139875 |
| 26 | miR-411 | 1.796262 | 0.007805 |
| 27 | miR-483-5p | 5.632765 | 0.1209546 |
| 28 | miR-20a | 3.08 | 1.99E-06 |
| 29 | miR-21 | 3.9 | 4.23E-05 |
| 30 | miR-24 | 2.54 | 0.002696 |
| 31 | miR-25 | 4.72 | 1.89E-08 |
| 32 | miR-26a | 4.16 | 6.34E-07 |
| 33 | miR-99 | 2.62 | 5.79E-05 |
| 34 | miR-122 | 3.26 | 0.000102 |
| 35 | miR-185 | 2.3 | 0.00055 |
| 36 | miR-191 | 2.91 | 0.000282 |

From the selected 36 up-regulated miRNAs in Table 3, according to the standard that average alteration-fold>2 and p value<0.01, 7 miRNAs are further selected preferably as the molecular marker for pancreatic cancer diagnosis, which are miR-20a, miR-21, miR-24, miR-25, miR-99, miR-185 and miR-191. Detailed results are shown in Table 4.

TABLE 4

7 miRNAs Selected

| | Concentration of miRNA in serum of control group (Mean ± SE) (fmol/L) | Concentration of miRNA in serum of lung cancer patients (Mean ± SE) (fmol/L) | Average alteration-fold | P value |
|---|---|---|---|---|
| miR-20a | 68.44 ± 9.46 | 214.68 ± 23.29 | 3.13 | 3.64E-07 |
| miR-21 | 8.82 ± 1.66 | 37.37 ± 5.87 | 4.24 | 2.28E-05 |
| miR-24 | 29.45 ± 4.64 | 78.78 ± 13.57 | 2.67 | 0.001255 |
| miR-25 | 5.02 ± 0.91 | 25.51 ± 2.54 | 5.08 | 8.18E-10 |
| miR-99 | 16.16 ± 3.64 | 43.09 ± 4.64 | 2.67 | 2.61E-05 |
| miR-185 | 22.08 ± 4.91 | 46.48 ± 6.74 | 2.10 | 0.007051 |
| miR-191 | 50.38 ± 11.85 | 144.70 ± 21.82 | 2.87 | 0.000372 |

Cluster analysis is conducted on the above-mentioned 7 miRNAs and the differential expression of these 7 miRNAs between the pancreatic cancer serum and the serum samples from normal controls is further demonstrated. The specific variation analysis results of the 7 miRNAs in serum/plasma which are used as specific fingerprint of pancreatic cancer in normal subjects and pancreatic cancer patients are shown in FIGS. 4A-D. It can be determined from the figures that the sample of pancreatic cancer patients and normal subjects can be distinguished definitely according to the combination of 7 miRNAs, and pancreatic cancer samples and chronic pancreatitis samples can also be distinguished, that is to say, the pancreatic cancer samples and control samples (including the normal subjects and the chronic pancreatitis patients) are distinguished definitely by 7 miRNAs.

The data process procedure of cluster analysis is as follows: for the training set (FIG. 4A, 25 patients and 25 controls), the validation set (FIG. 4B, 95 patients and 81 controls) and high risk samples (FIG. 4C, 95 pancreatic cancer patients and 82 chronic pancreatitis patients; and FIG. 4D, 95 patients with pancreatic cancer, 81 controls and 82 chronic pancreatitis). The absolute expression levels of these seven miRNAs of pancreatic cancer and control serum samples are compared and normalized, clustered and drawn as FIG. 4A-D (using software cluster 3.0). That is to say, the 7 miRNAs in serum/plasma are used as specific fingerprints of pancreatic cancers according to the analysis. The results are illustrated in details in FIGS. 4A-D.

Figure 4A:
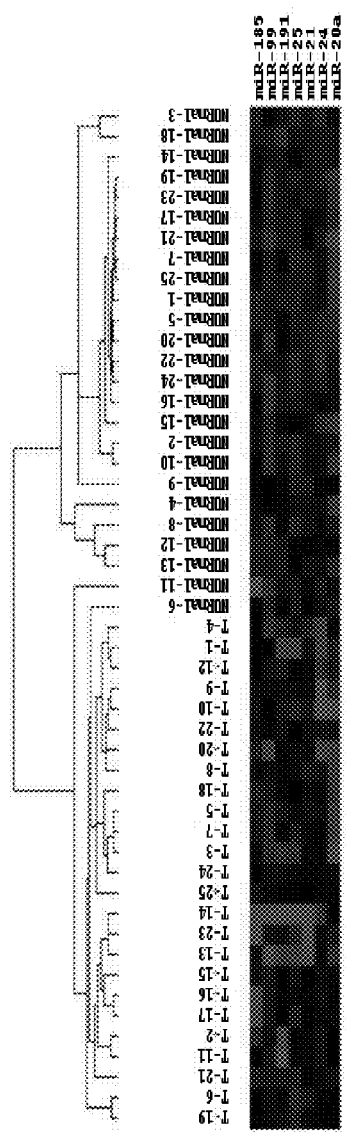
FIGS. 4A-4D show the cluster analysis results of 7 specific serum/plasma miRNAs from normal human subjects, chronic pancreatitis patients and pancreatic cancer patients.

In FIG. 4A, the tags at the right side represent the 7 miRNAs detected, and the tags above represent the individual samples detected, wherein "normal" represents the normal human subjects (n=25) which mostly locate in the right side of the figure, and "T" represents the pancreatic patients (n=25) which mostly locate in at the left side of the figure. This figure demonstrates that the detection of the expression levels of the 7 miRNAs can be used to distinguish the normal human subjects from the pancreatic cancer patients.

Figure 4B:
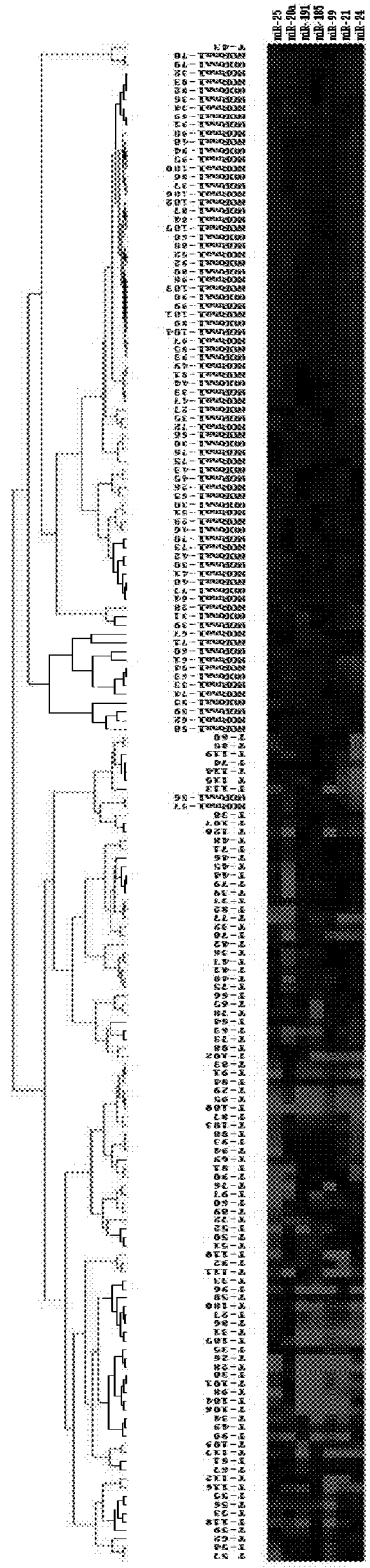

In FIG. 4B, the tags at the right side represent the 7 miRNAs detected, and the tags above represent the individual samples detected, wherein "normal" represents the normal human subjects (n=81) which mostly locate in the right side of the figure, and "T" represents the pancreatic cancer patients (n=95) which mostly locate in the left side of the figure. By enlarging the detection sample scale, this figure further demonstrates that the detection of the expression levels of the 7 miRNAs can be used to distinguish the normal human subjects from pancreatic cancer patients.

Figure 4C:
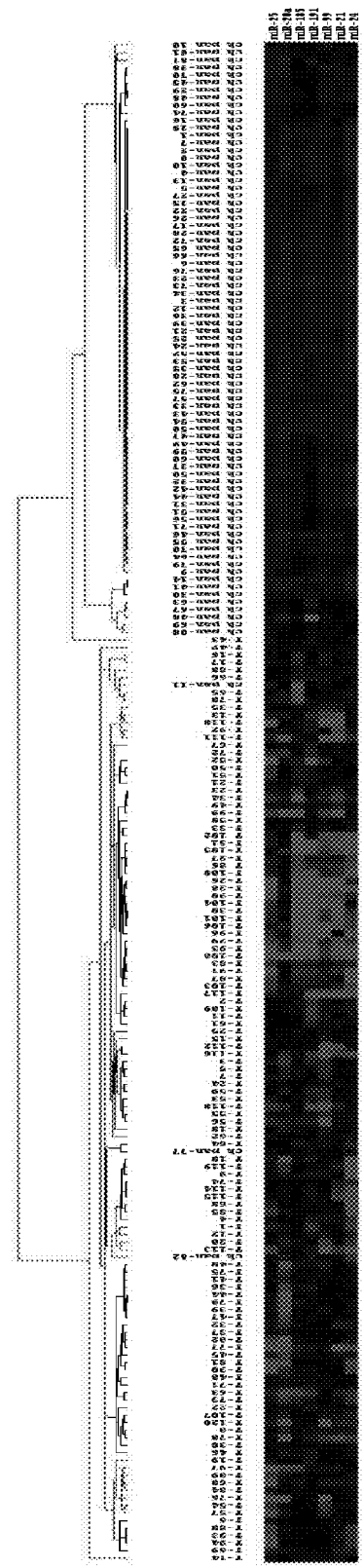

In FIG. 4C, the tags at the right side represent the 7 miRNAs detected, and the tags above represent the individual samples detected, and "ch pan" (represents chronic pancreatitis (n=82)) which mostly locate in the right side of the figure: and "T" represents the pancreatic cancer patients (n=120) which mostly locate in the left side of the figure. By enlarging the detection sample scale, the figure further demonstrates that the detection on the expression levels of the 7 miRNAs can be used to distinguish the chronic pancreatitis from pancreatic cancer patients.

Figure 4D:
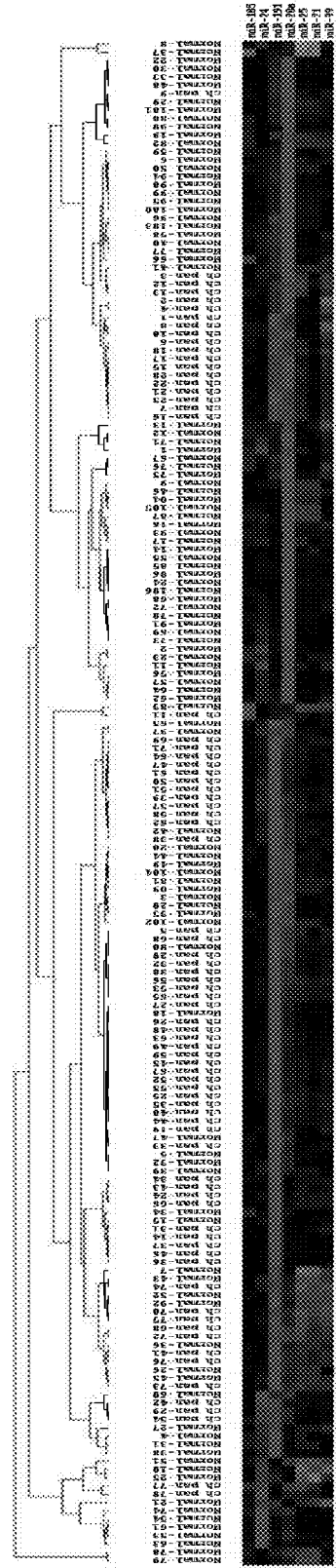

In FIG. 4D the tags at the right side represent the 7 miRNAs for detection; the tags above represent the individual samples for detection; wherein "nor" represent normal subjects (n=81); "ch pan" represent chronic pancreatitis patients (n=78); the samples of normal subjects and chronic pancreatitis patients mostly locate in discrete distribution. It can be seen that the 7 miRNAs can be used to distinguish the chronic pancreatitis patients from the controls (including the normal human subjects and chronic pancreatic patients).

Risk scoring analysis is performed for FIGS. 4A, 4B and 4D, and the results are shown in Table 5. In Table 5, in the first row, the risk scoring marks of the assessing samples are listed, and in the second to eighth rows, the number of pancreatic cancer patients, chronic pancreatitis patients, and normal subjects are listed respectively for the training set, the validation set and the pancreatic cancer patients which suffers from high risk. The statistical analysis is conducted with a statistical analysis software (SAS), and the risk scoring value is set as 6. If the risk scoring value of the sample is 6 then the sample is classified as of a pancreatic cancer patient; and if the risk scoring of the sample is <6, the sample is classified as of a normal human subject.

The specific statistical analysis is performed as follows: besides each variable being controlled during the whole process, all the data shall be standardized into a zero-mean and a standard deviation before clustering. In order to minimize the influence of the missing values and to assist the layering of the clustering and risk scoring, the KNN (K-Nearest Neighbors, a technique based on missing data imputation) technique is applied to estimate the missing values in the $19^{th}$-$20^{th}$ interval. For example, if a value is missing in the miRNAs of sample A, other K (number) miRNAs which are expressed at the same time shall be detected in the same sample, and the samples with the most similar miRNA expression to sample A shall be detected. The missing value can be estimated by computing the weighted average of the K most similar miRNAs in sample A. The weighted average computation takes the expression similarity of each miRNA as its weighted value. The K herein is set as 9, which means 9 neighboring miRNAs are included in the computation. Besides, the computation results obtained from the KNN technique have little effect on the current research conclusions, because the invocation rate of all markers is higher than 97.6%, and there is no sample missing two or more than two markers.

The layering of the clustering with the complete associated mode in cluster 3.0 is applied in the statistics. To conduct risk scoring, 95% of the upper limit of the value reference interval of each miRNA in the control set is set as t, being the threshold value controlling the expression level encoding of miRNAs from each sample. The risk scoring of each miRNA is denoted as S, which can be expressed with the equation:

$$s_{ij} = \begin{cases} 0 & \text{if } r_{ij} < t_j \\ 1 & \text{otherwise} \end{cases}$$

in which i stands for the $i^{th}$ sample, $\hat{j}$ stands for the $j^{th}$ miRNA. Considering that the assessment of the weighted values of the miRNA in pancreatic cancer is different, a risk scoring function is formed for each patient based on the linear combination of the miRNA expression levels. In accordance to the related materials of the K miRNAs, the risk scoring function of sample i is:

$$rsf_i = \Sigma_{j=1}^{k} \text{sign}_j \cdot W_j \cdot s_{ij}$$

wherein, sij is the risk scoring of miRNA $\hat{j}$ from sample i, and Ws is the weighted value of miRNA $\hat{j}$ in risk scoring. To determine sign and Ws, the fitting application with the Logistic Regression Model with 7 single variables is conducted on the subjects with risk scoring values. The regression coefficient of each risk scoring is used as the weighted value of each miRNA in the risk scoring function, and the sign in the regression coefficient determines the sign in the risk scoring function. The diagnosis effect of the sample set is evaluated with the frequency table and the ROC curve.

TABLE 5

Risk scoring of patients and controls (normal human subjects)

| | | Risk scoring | | | | | | |
|---|---|---|---|---|---|---|---|---|
| | | 0 | 0-3 | 3-6 | 6-9 | 9-12 | 12-15 | 15-18 |
| Training sets (FIG. 4A) | Normal | 19 | 2 | 4 | 0 | 0 | 0 | 0 |
| | Pancreatic cancer | 0 | 0 | 2 | 6 | 6 | 4 | 6 |
| Validation sets (FIG. 4B) | Normal | 60 | 5 | 10 | 4 | 2 | 0 | 0 |
| | Pancreatic cancer | 0 | 0 | 3 | 12 | 18 | 22 | 20 |
| High risk factor sets (FIG. 4C, 4D) | Normal | 79 | 7 | 14 | 4 | 2 | 0 | 0 |
| | Pancreatic cancer | 0 | 0 | 5 | 18 | 24 | 26 | 26 |
| | Pancreatitis | 70 | 3 | 2 | 0 | 2 | 3 | 0 |

| | | Risk scoring | | | Total | | |
|---|---|---|---|---|---|---|---|
| | | 18-21 | 21-24 | >24 | amount | PPV* | NPV** |
| Training sets (FIG. 4A) | Normal | 0 | 0 | 0 | 25 | 0 | 0.93 |
| | Pancreatic cancer | 1 | 0 | 0 | 25 | 1 | 0 |
| Validation sets (FIG. 4B) | Normal | 0 | 0 | 0 | 81 | 0 | 0.96 |
| | Pancreatic cancer | 12 | 8 | 0 | 95 | 0.93 | 0 |
| High risk factor sets (FIG. 4C, 4D) | Normal | 0 | 0 | 0 | 106 | 0 | 0.94 |
| | Pancreatic cancer | 13 | 8 | 0 | 120 | 0.96 | 0 |
| | Pancreatitis | 0 | 1 | 1 | 82 | 0 | 0.91 |

In this table,
*positive predictive value,
**negative predictive value

Figure 5A:
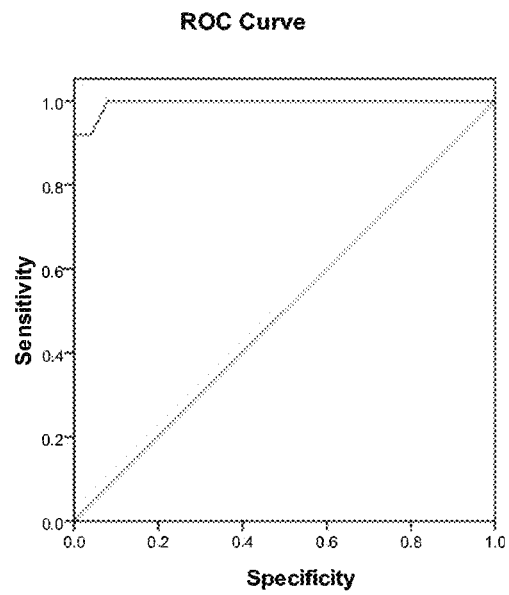
FIGS. 5A-5C are schematic illustrations of the sensitivity of the 7 specific miRNAs in the detection of pancreatic cancer.
Figure 5B:
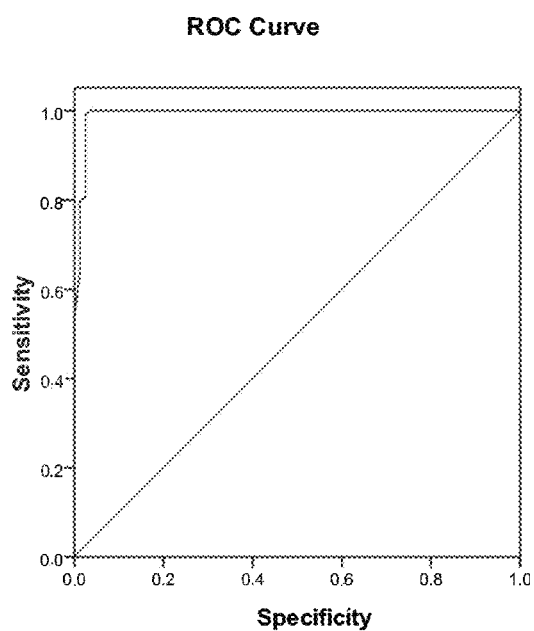
Figure 5C:
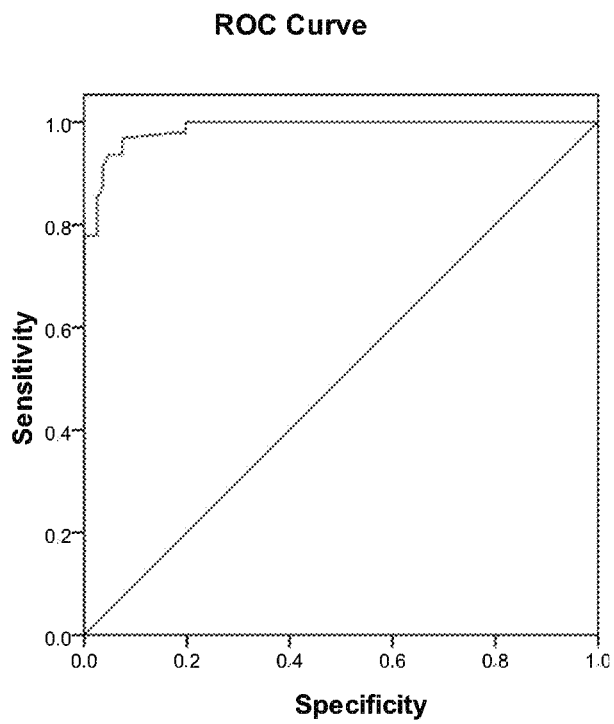

The sensitivity and specificity diagram of miRNA detecting pancreatic cancer is given in FIGS. 5A-C. If the total area (that is, the number of detecting samples) is one, we can see that the area under the curve (that is, credibility) corresponds to the training sets of FIG. 4A (FIG. 5A), corresponds to the validation sets of FIG. 4B (FIG. 5B) and corresponds to the high risk factor sets of FIGS. 4C and 4D (that is, including the samples of pancreatic cancers, normal subjects and chronic pancreatitis, FIG. 5C) reaching 0.995, 0.987 and 0.993, respectively.

Figure 6:
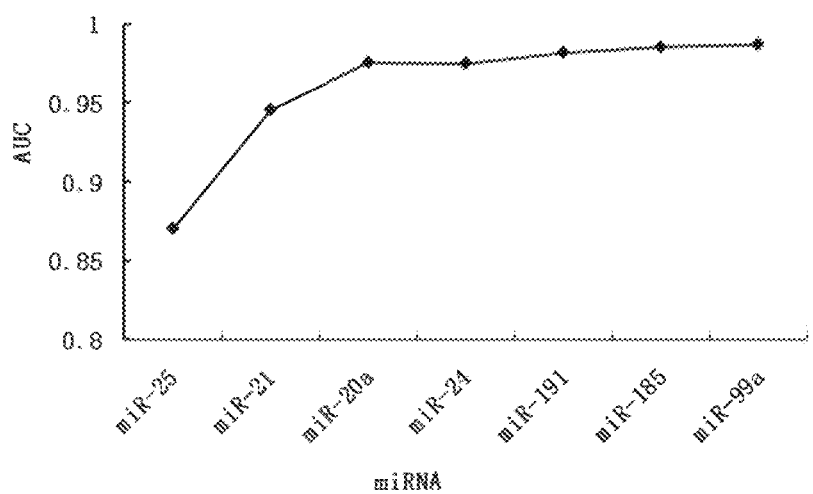
FIG. 6 is a result diagram of the accuracy of the 7 miRNAs in the detection of pancreatic cancer.

FIG. 6 shows the accuracy for results of the 7 miRNAs detecting pancreatic cancer. The abscissa is the species of detecting miRNA, and ordinate is the area under the curve, representing the accuracy of using 7 miRNAs to detect pancreatic cancer (given the total area (that is, the number of detecting samples) is one). We can see that the area under the curve (that is, accuracy)>0.98.

The invention claimed is:

1. A composition consisting of microRNA probes of nucleotide sequence SEQ ID NO: 31 and one or more of nucleotide sequences SEQ ID NO: 28, SEQ ID NO: 29, SEQ ID NO: 30, SEQ ID NO: 33, SEQ ID NO: 35 and SEQ ID NO: 36, wherein the microRNA probes are fluorescently or isotopically labeled, and wherein the composition optionally consists of one or more additional components other than microRNA probes.

2. A kit comprising the composition according to claim 1, a polymerase, and optionally a deoxyribonucleotide.

3. A method comprising:
   (a) obtaining a plasma or a serum sample from a human patient suspected of having pancreatic cancer or pancreatitis;
   (b) contacting the plasma or the serum, or RNA or cDNA derived therefrom, with the composition of claim 1; and
   (c) detecting the levels of miR-25 and one or more of miR-20a, miR-21, miR-24, miR-99, miR-185 and miR-191.

4. The method of claim 3, wherein said detecting the levels of miR-25 and one or more of miR-20a, miR-21, miR-24, miR-99, miR-185 and miR-191 is done by a real time RT-PCR assay comprising:
   (a) preparing at least one cDNA sample;
   (b) introducing the composition consisting of microRNA probes of nucleotide sequence SEQ ID NO: 31 and one or more of nucleotide sequences SEQ ID NO: 28, SEQ ID NO: 29, SEQ ID NO: 30, SEQ ID NO: 33, SEQ ID NO: 35 and SEQ ID NO: 36, wherein the microRNA probes are fluorescently labeled, and wherein the composition optionally consists of one or more additional components other than microRNA probes;
   (c) performing the real-time RT-PCR; and
   (d) detecting the levels of the microRNAs.

5. The method of claim 4, wherein step (a) comprises:
   (i) isolating total RNA from the patient's serum or plasma and preparing at least one cDNA sample by RNA reverse transcription; or
   (ii) collecting serum or plasma from the human patient and preparing at least one cDNA sample by reverse transcription with the serum or plasma functioning as a buffer solution for the reverse transcription.

6. The method of claim 3, wherein the amounts of microRNAs are determined by Northern blotting.

7. The method of claim 3, wherein the amounts of the microRNAs are determined by a RNase protection assay.

8. The method of claim 3, wherein the amounts of the microRNAs are determined by a hybridization assay.

9. The method of claim 3, wherein the serum or plasma is obtained from living bodies, tissues, organs, or corpses of human beings.

10. A method comprising:
  (a) measuring a first amount of microRNAs consisting of miR-25 and one or more of miR-20a, miR-21, miR-24, miR-99, miR-185 and miR-191 obtained from serum or plasma of a subject having pancreatic cancer or pancreatitis by contacting the serum or plasma, or RNA or cDNA derived therefrom, with the composition according to claim 1;
  (b) administering a drug candidate to the subject;
  (c) measuring a second amount of the microRNAs of step (a) in serum or plasma obtained from the subject treated with the drug candidate; and
  (d) comparing the first and second amounts of the microRNAs.

* * * * *

UNITED STATES PATENT AND TRADEMARK OFFICE
CERTIFICATE OF CORRECTION

PATENT NO. : 9,637,793 B2
APPLICATION NO. : 13/518801
DATED : May 2, 2017
INVENTOR(S) : Chenyu Zhang et al.

It is certified that error appears in the above-identified patent and that said Letters Patent is hereby corrected as shown below:

In Column 4 at Line 5, Change "used \to" to --used to--.

In Column 11 at Line 62, Change "100" to --10μl--.

In Column 12 at Line 59, Change "mR-181a," to --miR-181a,--.

In Column 16 at Line 61, Change "FIG." to --FIGS.--.

In Column 17 at Line 47, Change "is 6" to --is≥6--.

In Column 18 at Line 50, Change "(FIG." to --(FIGS.--.

In Column 18 at Line 62, Change "(FIG." to --(FIGS.--.

Signed and Sealed this
Eighth Day of May, 2018

Andrei Iancu
*Director of the United States Patent and Trademark Office*

SEQUENCE LISTING

<160> NUMBER OF SEQ ID NOS: 36

<210> SEQ ID NO 1
<211> LENGTH: 21
<212> TYPE: DNA
<213> ORGANISM: Artificial Sequence
<220> FEATURE:
<223> OTHER INFORMATION: probe

<400> SEQUENCE: 1
gcggaactta gccactgtga a                                         21

<210> SEQ ID NO 2
<211> LENGTH: 21
<212> TYPE: DNA
<213> ORGANISM: Artificial Sequence
<220> FEATURE:
<223> OTHER INFORMATION: probe

<400> SEQUENCE: 2
gcagaactta gccactgtga a                                         21

<210> SEQ ID NO 3
<211> LENGTH: 21
<212> TYPE: DNA
<213> ORGANISM: Artificial Sequence
<220> FEATURE:
<223> OTHER INFORMATION: probe

<400> SEQUENCE: 3
aaccgatttc agatggtgct a                                         21

<210> SEQ ID NO 4
<211> LENGTH: 20
<212> TYPE: DNA
<213> ORGANISM: Artificial Sequence
<220> FEATURE:
<223> OTHER INFORMATION: probe

<400> SEQUENCE: 4
accgatttca aatggtgcta                                           20

<210> SEQ ID NO 5
<211> LENGTH: 22
<212> TYPE: DNA
<213> ORGANISM: Artificial Sequence
<220> FEATURE:
<223> OTHER INFORMATION: probe

<400> SEQUENCE: 5
cttccagtcg aggatgttta ca                                        22

<210> SEQ ID NO 6
<211> LENGTH: 22
<212> TYPE: DNA

```
<213> ORGANISM: Artificial Sequence
<220> FEATURE:
<223> OTHER INFORMATION: probe

<400> SEQUENCE: 6
cttccagtcg gggatgttta ca                                              22

<210> SEQ ID NO 7
<211> LENGTH: 19
<212> TYPE: DNA
<213> ORGANISM: Artificial Sequence
<220> FEATURE:
<223> OTHER INFORMATION: probe

<400> SEQUENCE: 7
caatgcaact acaatgcac                                                  19

<210> SEQ ID NO 8
<211> LENGTH: 21
<212> TYPE: DNA
<213> ORGANISM: Artificial Sequence
<220> FEATURE:
<223> OTHER INFORMATION: probe

<400> SEQUENCE: 8
caggccggga caagtgcaat a                                               21

<210> SEQ ID NO 9
<211> LENGTH: 22
<212> TYPE: DNA
<213> ORGANISM: Artificial Sequence
<220> FEATURE:
<223> OTHER INFORMATION: probe

<400> SEQUENCE: 9
cacaagttcg gatctacggg tt                                              22

<210> SEQ ID NO 10
<211> LENGTH: 22
<212> TYPE: DNA
<213> ORGANISM: Artificial Sequence
<220> FEATURE:
<223> OTHER INFORMATION: probe

<400> SEQUENCE: 10
cttcagttat cacagtactg ta                                              22

<210> SEQ ID NO 11
<211> LENGTH: 23
<212> TYPE: DNA
<213> ORGANISM: Artificial Sequence
<220> FEATURE:
<223> OTHER INFORMATION: probe

<400> SEQUENCE: 11
tcatagccct gtacaatgct gct                                             23

<210> SEQ ID NO 12
<211> LENGTH: 22
<212> TYPE: DNA
<213> ORGANISM: Artificial Sequence
<220> FEATURE:
<223> OTHER INFORMATION: probe

<400> SEQUENCE: 12
tcacaagtta gggtctcagg ga                                              22
```

```
<210> SEQ ID NO 13
<211> LENGTH: 22
<212> TYPE: DNA
<213> ORGANISM: Artificial Sequence
<220> FEATURE:
<223> OTHER INFORMATION: probe

<400> SEQUENCE: 13
atgccctttc atcattgcac tg                                                  22

<210> SEQ ID NO 14
<211> LENGTH: 21
<212> TYPE: DNA
<213> ORGANISM: Artificial Sequence
<220> FEATURE:
<223> OTHER INFORMATION: probe

<400> SEQUENCE: 14
ctaccatagg gtaaaaccac t                                                   21

<210> SEQ ID NO 15
<211> LENGTH: 22
<212> TYPE: DNA
<213> ORGANISM: Artificial Sequence
<220> FEATURE:
<223> OTHER INFORMATION: probe

<400> SEQUENCE: 15
acaaagttct gtagtgcact ga                                                  22

<210> SEQ ID NO 16
<211> LENGTH: 21
<212> TYPE: DNA
<213> ORGANISM: Artificial Sequence
<220> FEATURE:
<223> OTHER INFORMATION: probe

<400> SEQUENCE: 16
ggctgtcaat tcataggtca g                                                   21

<210> SEQ ID NO 17
<211> LENGTH: 23
<212> TYPE: DNA
<213> ORGANISM: Artificial Sequence
<220> FEATURE:
<223> OTHER INFORMATION: probe

<400> SEQUENCE: 17
gaacaggtag tctgaacact ggg                                                 23

<210> SEQ ID NO 18
<211> LENGTH: 22
<212> TYPE: DNA
<213> ORGANISM: Artificial Sequence
<220> FEATURE:
<223> OTHER INFORMATION: probe

<400> SEQUENCE: 18
aaccaatgtg cagactactg ta                                                  22

<210> SEQ ID NO 19
<211> LENGTH: 24
<212> TYPE: DNA
<213> ORGANISM: Artificial Sequence
<220> FEATURE:
```

<223> OTHER INFORMATION: probe

<400> SEQUENCE: 19
gagacccagt agccagatgt agct                                        24

<210> SEQ ID NO 20
<211> LENGTH: 22
<212> TYPE: DNA
<213> ORGANISM: Artificial Sequence
<220> FEATURE:
<223> OTHER INFORMATION: probe

<400> SEQUENCE: 20
tcagccgctg tcacacgcac ag                                          22

<210> SEQ ID NO 21
<211> LENGTH: 21
<212> TYPE: DNA
<213> ORGANISM: Artificial Sequence
<220> FEATURE:
<223> OTHER INFORMATION: probe

<400> SEQUENCE: 21
gtctgtcaat tcataggtca t                                           21

<210> SEQ ID NO 22
<211> LENGTH: 21
<212> TYPE: DNA
<213> ORGANISM: Artificial Sequence
<220> FEATURE:
<223> OTHER INFORMATION: probe

<400> SEQUENCE: 22
ggggtatttg acaaactgac a                                           21

<210> SEQ ID NO 23
<211> LENGTH: 23
<212> TYPE: DNA
<213> ORGANISM: Artificial Sequence
<220> FEATURE:
<223> OTHER INFORMATION: probe

<400> SEQUENCE: 23
ttcgccctct caacccagct ttt                                         23

<210> SEQ ID NO 24
<211> LENGTH: 22
<212> TYPE: DNA
<213> ORGANISM: Artificial Sequence
<220> FEATURE:
<223> OTHER INFORMATION: probe

<400> SEQUENCE: 24
gtacccctgg agattctgat aa                                          22

<210> SEQ ID NO 25
<211> LENGTH: 22
<212> TYPE: DNA
<213> ORGANISM: Artificial Sequence
<220> FEATURE:
<223> OTHER INFORMATION: probe

<400> SEQUENCE: 25
acacaggacc tggagtcagg ag                                          22

```
<210> SEQ ID NO 26
<211> LENGTH: 21
<212> TYPE: DNA
<213> ORGANISM: Artificial Sequence
<220> FEATURE:
<223> OTHER INFORMATION: probe

<400> SEQUENCE: 26
cgtacgctat acggtctact a                                              21

<210> SEQ ID NO 27
<211> LENGTH: 23
<212> TYPE: DNA
<213> ORGANISM: Artificial Sequence
<220> FEATURE:
<223> OTHER INFORMATION: probe

<400> SEQUENCE: 27
agaagacggg aggagaggag tga                                            23

<210> SEQ ID NO 28
<211> LENGTH: 23
<212> TYPE: DNA
<213> ORGANISM: Artificial Sequence
<220> FEATURE:
<223> OTHER INFORMATION: probe

<400> SEQUENCE: 28
ctacctgcac tataagcact tta                                            23

<210> SEQ ID NO 29
<211> LENGTH: 22
<212> TYPE: DNA
<213> ORGANISM: Artificial Sequence
<220> FEATURE:
<223> OTHER INFORMATION: probe

<400> SEQUENCE: 29
tcaacatcag tctgataagc ta                                             22

<210> SEQ ID NO 30
<211> LENGTH: 22
<212> TYPE: DNA
<213> ORGANISM: Artificial Sequence
<220> FEATURE:
<223> OTHER INFORMATION: probe

<400> SEQUENCE: 30
ctgttcctgc tgaactgagc ca                                             22

<210> SEQ ID NO 31
<211> LENGTH: 22
<212> TYPE: DNA
<213> ORGANISM: Artificial Sequence
<220> FEATURE:
<223> OTHER INFORMATION: probe

<400> SEQUENCE: 31
tcagaccgag acaagtgcaa tg                                             22

<210> SEQ ID NO 32
<211> LENGTH: 21
<212> TYPE: DNA
<213> ORGANISM: Artificial Sequence
<220> FEATURE:
<223> OTHER INFORMATION: probe
```

```
<400> SEQUENCE: 32
gcctatcctg gattacttga a                                              21

<210> SEQ ID NO 33
<211> LENGTH: 22
<212> TYPE: DNA
<213> ORGANISM: Artificial Sequence
<220> FEATURE:
<223> OTHER INFORMATION: probe

<400> SEQUENCE: 33
cacaagatcg gatctacggg tt                                             22

<210> SEQ ID NO 34
<211> LENGTH: 23
<212> TYPE: DNA
<213> ORGANISM: Artificial Sequence
<220> FEATURE:
<223> OTHER INFORMATION: probe

<400> SEQUENCE: 34
acaaacacca ttgtcacact cca                                            23

<210> SEQ ID NO 35
<211> LENGTH: 18
<212> TYPE: DNA
<213> ORGANISM: Artificial Sequence
<220> FEATURE:
<223> OTHER INFORMATION: probe

<400> SEQUENCE: 35
gaactgcctt tctctcca                                                  18

<210> SEQ ID NO 36
<211> LENGTH: 22
<212> TYPE: DNA
<213> ORGANISM: Artificial Sequence
<220> FEATURE:
<223> OTHER INFORMATION: probe

<400> SEQUENCE: 36
agctgctttt gggattccgt tg                                             22
```